United States Patent
Kim et al.

(10) Patent No.: US 9,585,573 B2
(45) Date of Patent: Mar. 7, 2017

(54) APPARATUS AND METHOD FOR ESTIMATING BLOOD PRESSURE BY USING VARIABLE CHARACTERISTIC RATIO

(75) Inventors: Seok Chan Kim, Seoul (KR); Youn-ho Kim, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 1031 days.

(21) Appl. No.: 12/723,931

(22) Filed: Mar. 15, 2010

(65) Prior Publication Data

US 2010/0298721 A1 Nov. 25, 2010

(30) Foreign Application Priority Data

May 22, 2009 (KR) ........................ 10-2009-0045202

(51) Int. Cl.
A61B 5/02 (2006.01)
A61B 5/022 (2006.01)
A61B 5/021 (2006.01)

(52) U.S. Cl.
CPC .......... *A61B 5/022* (2013.01); *A61B 5/02108* (2013.01); *A61B 5/02225* (2013.01)

(58) Field of Classification Search
USPC ........................................................ 600/485
See application file for complete search history.

(56) References Cited

U.S. PATENT DOCUMENTS

| | | | |
|---|---|---|---|
| 4,464,123 A * | 8/1984 | Glover et al. ................. 434/268 |
| 5,339,818 A * | 8/1994 | Baker et al. ................... 600/490 |
| 5,577,508 A * | 11/1996 | Medero ......................... 600/494 |
| 6,517,495 B1 | 2/2003 | Hersh | |
| 6,733,462 B1 * | 5/2004 | Frick .................. A61B 5/02156 600/485 |
| 7,341,560 B2 * | 3/2008 | Henderson et al. .......... 600/500 |
| 2003/0045801 A1 * | 3/2003 | Chen et al. .................... 600/494 |

FOREIGN PATENT DOCUMENTS

| | | |
|---|---|---|
| JP | 2001-178693 A | 7/2001 |
| JP | 2006075437 A | 3/2006 |
| JP | 2006-247220 A | 9/2006 |
| JP | 2006-255096 A | 9/2006 |
| JP | 2006-340896 A | 12/2006 |
| JP | 2007082682 A | 4/2007 |

(Continued)

OTHER PUBLICATIONS

Primer on Absolute vs. Relative Differences, 2013, American College of Physicians.*

(Continued)

*Primary Examiner* — Navin Natnithithadha
*Assistant Examiner* — Michael R Bloch
(74) *Attorney, Agent, or Firm* — Cantor Colburn LLP

(57) ABSTRACT

Provided is a method for estimating blood pressure using a variable characteristic ratio. In the method, a pressure wave detected at a measurement body part of a subject is obtained to calculate a characteristic ratio of the subject based on a correlation between the characteristic ratio used to determine blood pressure at a measurement body part and the shape of the pressure wave detected at the measurement body part. The blood pressure at the measurement body part of the subject is estimated using the calculated characteristic ratio.

18 Claims, 9 Drawing Sheets

(56) References Cited

FOREIGN PATENT DOCUMENTS

KR  1020060111414 A  10/2006
KR  1020080040593 A  5/2008

OTHER PUBLICATIONS

Ursino, et al., "A Mathematical Study of Some Biomechanical Factors Affecting the Oscillometric Blood Pressure Measurement", IEEE Transactions on Biomedical Engineering, vol. 43, No. 8, Aug. 1996, pp. 761-778.
Korean Office Action with English Translation for Application No. 10-2009-0045202 dated May 8, 2015.

* cited by examiner

APPARATUS AND METHOD FOR ESTIMATING BLOOD PRESSURE BY USING VARIABLE CHARACTERISTIC RATIO

CROSS-REFERENCE TO RELATED APPLICATION

This application claims priority to Korean Patent Application No. 10-2009-0045202, filed on May 22, 2009, and all the benefits accruing therefrom under 35 U.S.C. §119, the content of which in its entirety is herein incorporated by reference.

BACKGROUND

1. Field

Provided is an apparatus and method for estimating blood pressure using variable characteristic ratios.

2. Description of the Related Art

Blood pressure is used as an index of the health condition of a person. Apparatuses for measuring blood pressure are commonly used in medical institutions and at home. The United States Food and Drug Administration ("FDA") determines the standards required for apparatuses for measuring blood pressure, specifically the FDA requires blood pressure measuring apparatuses to comply with the requirements of the Association for the Advancement of Medical Instrumentation ("AAMI"). The American National Standards Institute ("ANSI")/AAMI SP10 issued by the AAMI offers specification details, and safety and performance requirements for the blood pressure measuring apparatuses.

In order to measure systolic blood pressure, pressure is applied to stop the flow of blood through a site where arterial blood flows. The pressure is then slowly released and the pressure at which an initial pulse sound is heard is the systolic blood pressure. A diastolic blood pressure is the pressure where the pulse sound disappears. Digital hemadynamometers calculate blood pressure by detecting a waveform corresponding to a pressure measured while pressurizing a blood vessel.

SUMMARY

Provided is a blood pressure estimating apparatus and method in which a variable characteristic ratio according to the physical characteristics of a subject is calculated, and accurate blood pressure estimation based on the calculated characteristic ratio is ensured.

Provided is a computer readable recording medium having recorded thereon a computer program for executing the method.

Blood pressure estimating apparatus and method are not limited to that described above, and may also include other aspects. These and other aspects will become more fully apparent from the following description or may be leaned by practice of the presented descriptions, as will be apparent to those of ordinary skill in the art.

Provided is a method of estimating blood pressure, the method including; obtaining a pressure wave detected at a measurement body part of a subject, calculating a characteristic ratio of the subject according to a shape of the obtained pressure wave based on a correlation between the characteristic ratio used to determine blood pressure at a measurement body part and the shape of the pressure wave detected at the measurement body part, and estimating blood pressure at the measurement body part of the subject using the calculated characteristic ratio.

Provided is a computer readable recording medium having embodied thereon a program for executing the method described above.

Provided is a blood pressure estimating apparatus including; a detection unit which detects a pressure wave at a measurement body part of a subject, a characteristic ratio calculation unit which calculates a characteristic ratio of the subject according to a shape of the detected pressure wave based on a correlation between a characteristic ratio used to determine blood pressure at a measurement body part and the shape of the detected pressure wave at the measurement body part, and a blood pressure estimating unit which estimates blood pressure at the measurement body part of the subject using the calculated characteristic ratio.

BRIEF DESCRIPTION OF THE DRAWINGS

These and/or other aspects will become apparent and more readily appreciated from the following description, taken in conjunction with the accompanying drawings of which.

DETAILED DESCRIPTION

Figure 1:
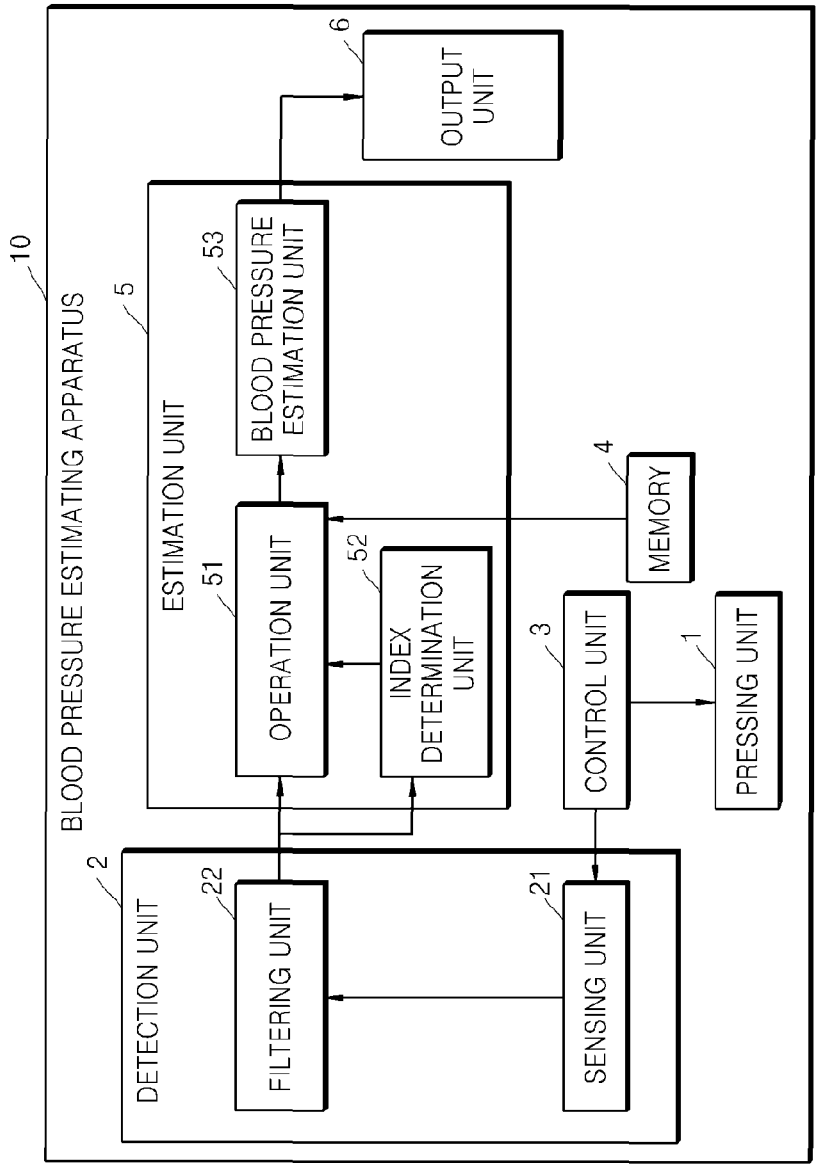
FIG. 1 is a diagram illustrating an embodiment of a configuration of a blood pressure estimating apparatus.

Embodiments now will be described more fully hereinafter with reference to the accompanying drawings, in which embodiments are shown. The embodiments may, however, be embodied in many different forms and should not be construed as limited to the embodiments set forth herein. Rather, these embodiments are provided so that this disclosure will be thorough and complete, and will fully convey the scope of the embodiments to those skilled in the art. Like reference numerals refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings disclosed herein.

The terminology used herein is for the purpose of describing particular embodiments only and is not intended to be limiting thereof. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on the scope thereof unless otherwise claimed. No language in the specification should be construed as indicating any non-claimed element as essential to the practice of the embodiments as used herein.

Hereinafter, the embodiments will be described in detail with reference to the accompanying drawings.

FIG. 1 is a diagram illustrating a configuration of an embodiment of a blood pressure estimating apparatus 10. Referring to FIG. 1, the blood pressure estimating apparatus 10 includes a pressing unit 1, a detection unit 2, a control unit 3, a memory 4, an estimation unit 5 and an output unit 6. Embodiments include configurations wherein the estimation unit 5 for estimating blood pressure is included in a blood pressure instrument, a blood pressure meter, a blood pressure measuring device or a hemadynamometer, although the present disclosure is not limited thereto. For example, embodiments also include configurations wherein the estimation unit 5 may be separated from such a blood pressure measuring apparatus as an independent blood pressure estimation device. In the present specification, only hardware components that are related to the embodiment of an apparatus for estimating the blood pressure will be described in order to prevent making the features of the blood pressure estimating apparatus 10 vague. However, it will be understood by one of ordinary skill in the art that any other general-use hardware components may also be included in addition to the hardware components illustrated in FIG. 1.

The blood pressure estimating apparatus 10 senses a pressure wave at a measurement body part of a subject, e.g., an arm of a subject, while the measurement body part is being pressed, i.e., has pressure applied thereto, for example by an arm cuff, calculates a characteristic ratio that varies according to the shape of the pressure wave, and estimates blood pressure of the subject based on the calculated characteristic ratio. The estimated blood pressure may include at least one selected from the group consisting of diastolic blood pressure and systolic blood pressure. In addition, the measurement body part may be any body part, such as an upper arm, a wrist, a finger, etc., and the pressure wave may include a pressure wave measured at the aorta, the brachial artery, the radial artery, etc. within the measurement body part. Characteristic ratios refer to ratios of amplitude with respect to the maximum amplitude of a pressure wave used to determine systolic blood pressure and diastolic blood pressure. In an embodiment of a blood pressure estimating method, blood pressure may be estimated using the characteristic ratio that varies depending on race, gender, age, physical conditions, arterial elasticity, etc., thereby improving accuracy in blood pressure estimation.

As blood is pumped around the human body by the heart, a pressure wave may be measured with respect to blood within blood vessels using the blood pressure estimating apparatus 10. The blood pressure is pressure on the walls of blood vessels as blood pumped out of the heart flows along the blood vessels, and includes arterial blood pressure, capillary blood pressure and venous blood pressure, according to the blood vessels where blood pressure is measured. The blood pressure varies periodically with the pulse, that is, the beating of the heart, e.g., according to the rhythmic heartbeats. Also, the blood pressure includes systolic blood pressure when blood flows into the arteries while the ventricles of the heart contract and diastolic blood pressure on the arterial walls due to the elasticity of the arterial walls even when the ventricles expand and blood stays in the ventricles.

An sphygmus wave is a wave generated as a pulse reaches peripheral nerves of the heart. The pulse is a phenomenon whereby the pressure of blood flowing into the aorta due to heartbeats affects other arteries throughout the body of the subject. That is, whenever the heart contracts, blood is provided from the heart to every part of the human body through the aorta and the pressure on the aorta varies accordingly. For example, the variation in pressure is transferred to peripheral arterioles of the hands and feet. The sphygmus wave represents the variation in pressure as a waveform. It will be understood by one of ordinary skill in the art that the blood pressure estimating apparatus 10 may measure at least one selected from the group consisting of the sphygmus wave and the pressure on the walls of the blood vessels in order to measure the blood pressure. Hereinafter, for convenience of explanation, a blood pressure measuring method is a method of measuring at least one selected from the group consisting of blood pressure and an sphygmus wave.

A blood pressure measuring apparatus may measure blood pressure by using at least one of an invasive method and a noninvasive method. The invasive method involves directly inserting a catheter into a blood vessel, and connecting the catheter to a manometer to measure the blood pressure. The noninvasive method involves winding a pressing member, for example, a cuff, around one part, such as an upper arm, to measure blood pressure, pumping air into the cuff to press the upper arm, and measuring blood pressure when blood in a brachial artery or a radial artery stops flowing. In the noninvasive method, the blood pressure is measured from outside the blood vessels. Due to the non-invasive nature of the noninvasive method, it is often the easiest and least painful method of measuring blood pressure.

Although the invasive method includes the direct insertion of the catheter into the blood vessel, the blood pressure may be accurately and continuously measured. Examples of the noninvasive method include an auscultatory method of measuring blood pressure using Korotkoff sounds, an oscillometric method of measuring blood pressure using oscillations generated due to the flow of blood, a tonometeric method using a tonometer, a method using pulse transit time ("PTT") and various other similar methods.

Although highly accurate, a blood pressure measuring method using the invasive method involves the insertion of a catheter into a blood vessel to measure blood pressure, a method which may cause some discomfort to the subject. However, the blood pressure estimating apparatus 10 may conveniently measure blood pressure using the noninvasive method and may increase the accuracy of measuring blood pressure using the variable characteristics ratios according to the shape of wave detected at a measurement body part of the subject. The estimation unit 5 estimates blood pressure using the characteristic ratios which vary according to the shape of the pressure wave detected while the measurement body part of the subject is being subjected to pressure. The measurement body part of the subject refers to a body part from which blood pressure is to be estimated using the blood pressure estimating apparatus 10, and examples of the measurement body part may include an upper arm, a wrist, a finger, etc. In detail, a pressure wave is detected at the aorta, the brachial artery, the radial artery, etc. within the measurement body part of the subject, and blood pressure is estimated by using the variable characteristic ratios, which vary according to the shape of the detected pressure wave.

With regard to the noninvasive method, in the auscultatory method, a body part where arterial blood flows is pressed sufficiently to stop the flow of arterial blood and then is released. The systolic blood pressure is measured as a pressure at a moment when an initial pulse is heard after beginning the release of the pressure and the diastolic blood pressure is measured as a pressure at a moment when no more pulse is heard after beginning the release of the pressure.

The oscillometric method and the tonometric method are used in digital blood pressure measuring apparatuses. Like the auscultatory method, in the oscillometric method, the systolic blood pressure and the diastolic blood pressure are measured by sensing oscillations of blood vessels, which are generated when a body part is pressed sufficiently to stop the flow of arterial blood and then is released. Pressure at regular ratios of amplitude with respect to a maximum amplitude of the oscillations of the blood vessels may be measured as the systolic blood pressure and the diastolic blood pressure. In the tonometric method, blood pressure may be continuously measured using the amplitude and shape of a sphygmus wave generated when pressure not entirely sufficient to completely stop the flow of arterial blood is applied to a body part.

A convenient and portable digital automatic hemadynamometer measures blood pressure using the noninvasive method. Blood pressure is measured using the magnitude of a pressure wave and a change in the pressure wave while a measurement body part is being pressed, e.g., by a cuff. Examples of the digital automatic hemadynamometer include a wrist-type hemadynamometer, a finger-type hemadynamometer, etc. according to the particular body parts to be pressed.

It will be understood by one of ordinary skill in the art that the blood pressure estimating apparatus 10 may be applied to all blood pressure measuring methods using the noninvasive method, and may be used to increase the accuracy of blood pressure measurements taken using, for example, a wrist-type or finger-type hemadynamometer. Thus, the accuracy of a wrist-type hemadynamometer, a finger-type hemadynamometer, etc. may be increased without adding additional hardware.

The pressing unit 1 presses a measurement body part at which blood pressure is to be measured. Embodiments of the pressing unit 1 may include a pressing element, for example, a cuff or a wrist band, etc., for pressing the measurement body part, and an actuator for driving the pressing element to expand or contract. The measurement body part includes any body part at which blood pressure is measurable using the above-described blood pressure measuring methods, such as an upper arm having the brachial artery therein, or a wrist having the radial artery therein. Embodiments also include configurations where the pressing unit 1 may be controlled by the control unit 3. The pressing unit 1 allows the pressing element 1 to expand or contract using the actuator so as to press the measurement body part at which blood pressure is to be measured, such as an upper arm, a wrist, or a finger.

The detection unit 2 detects a pressure wave at the measurement body part of the subject to be measured. Referring to FIG. 1, the embodiment of a detection unit 2 includes a sensing unit 21 and a filtering unit 22. The sensing unit 21 senses a pressure wave and a sphygmus wave in a blood vessel in the pressed measurement body part using at least one sensor while the measurement body part is being pressed. Although a pressure sensor, a photoplethysmography ("PPG") sensor, etc. may be generally used as the sensor, the sensing unit 21 is not limited thereto. For example, the sensor may be any apparatus for detecting pressure waves in a blood vessel.

In more detail, the pressing unit 1 gradually increases the pressure applied to press the measurement body part and then releases the pressure on the measurement body part. The pressure value at which the applied pressure stops is a value corresponding to when the flow of arterial blood stops and may be set by a user according to a usage environment. The sensing unit 21 senses a pressure wave in the blood vessel of the pressed body part of the subject. The sensing unit 21 senses a pressure wave and a sphygmus wave in the blood vessel of the pressed body part for a period of time, from before, or during, when the pressing unit 1 presses the body part until after the pressing unit 1 stops pressing the measurement body part. The period of time for sensing may be set by a user and may be generally set to be a period from when arterial blood stops flowing until when arterial blood normally circulates. The sensing unit 21 measures a pressure wave in the blood vessel and transmits the measured pressure wave to the filtering unit 22.

The filtering unit 22 separately passes high-frequency band components and low-frequency band components of the pressure wave sensed by the sensing unit 21, and transmits a waveform to be used in blood pressure estimation to the estimation unit 5. The embodiment of a filtering unit 22 includes a high-pass filter that passes a higher-frequency signal than a cutoff frequency without attenuation and attenuates a lower-frequency signal than the cutoff frequency, and a low-pass filter that passes a lower-frequency signal than the cutoff frequency without attenuation and attenuates a higher-frequency signal than the cutoff frequency. Alternative embodiments of the filtering unit 22 may include only one or the other of the high-pass filter and the low-pass filter.

Figure 2A:
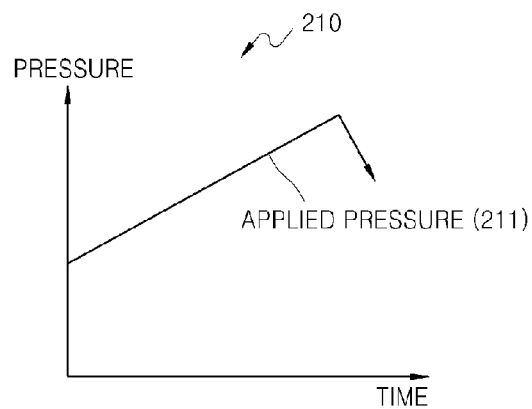
FIGS. 2A to 2C are diagrams describing waveforms filtered by an embodiment of a filtering unit.
Figure 2B:
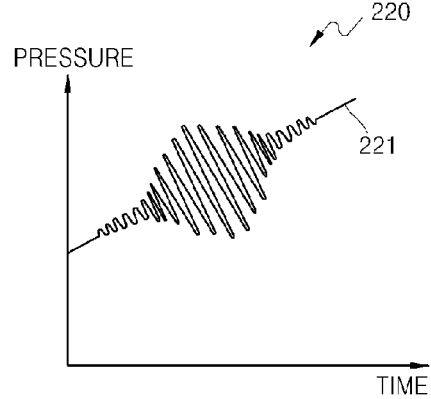
Figure 2C:
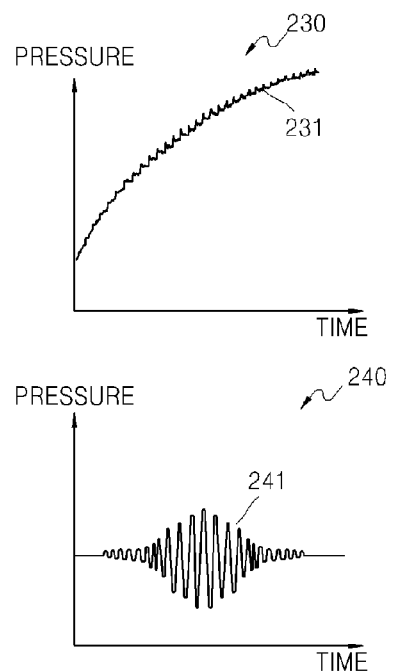

The filtering unit 22 will be described in more detail below. FIGS. 2A to 2C are diagrams describing waveforms filtered by the filtering unit 22. Referring to FIGS. 2A to 2C, FIG. 2A illustrates a graph 210 of pressure applied to press a measurement body part, FIG. 2B illustrates a graph 220 of a pressure wave sensed at the measurement body part, and FIG. 2C illustrates graphs 230 and 240 of the waveforms filtered by the filtering unit 22, are illustrated.

The graph 210 of applied pressure illustrates a condition for increasing the pressure applied to the measurement body part at which blood pressure is measured by the pressing unit 1. As described above, pressure 211 applied by the pressing unit 1 is continuously increased and then is released. Here, the pressure at which pressing stops may be varied according to a usage environment. The pressing unit 1 applying pressure to the measurement body part stops pressing when the pressing unit 1 reaches a pressure of 140 mm Hg at which blood vessels are occluded.

The graph 220 illustrates a waveform 221 sensed by the sensing unit 21, i.e., a sphygmus wave and a pressure wave. The waveform 221 sensed by the sensing unit 21 includes both high-frequency band components and low-frequency band components. The high-pass filter of the filtering unit 22 passes high-frequency band components (for example, a signal in a frequency band of about 0.5 Hz to about 30 Hz) and attenuates low-frequency band components. The low-frequency filter of the filtering unit 22 passes low-frequency band components (for example, a signal in a frequency band of less than about 0.5 Hz) and attenuates high-frequency band components. Thus, the wave form 221 sensed by the sensing unit 21 is filtered by the filtering unit 22 so as to form a filtered waveform 231 having the low-frequency components and a filtered waveform 241 having the high-frequency components. The blood pressure estimating apparatus 10 uses the filtered waveform 241 having the high-frequency components, and thus, hereinafter, for convenience of explanation, the filtered waveform 241 having the high-frequency components will be referred to as the waveform filtered by the filtering unit 22. The filtering unit 22 may include a general high-pass filter and low-pass filter, which are well known to one of ordinary skill in the art, and thus a detailed description thereof will not be provided here.

Referring back to FIG. 1, the control unit 3 controls the pressing unit 1 and the sensing unit 21. If a user operates the blood pressure estimating apparatus 10, the control unit 3 obtains a signal input from the user, generates a control signal, and thus operates the pressing unit 1 and the sensing unit 21. In addition to the pressing unit 1 and the sensing unit 21, the control unit 3 may also control the other components of the blood pressure estimating apparatus 10. Embodiments include configurations wherein the control unit 3 may correspond to one or a plurality of processors of the blood pressure estimating apparatus 10. A processor may be formed using an array of a plurality of logic gates, or a combination of a general-use microprocessor and memory for storing a computer program to be executed in the microprocessor. Also, it will be understood by one of ordinary skill in the art that the processor may be formed using a different type of hardware.

In the present embodiment, the memory 4 is a general storage medium that stores a relational equation of a plurality of data representing a correlation between a characteristic ratio, which is used to determine estimate blood pressure at a body part of a subject using measured blood pressure of the subject, and a shape of a pressure wave measured at the body part of the subject while the body part is being pressed. A relational equation of a plurality of data points may be derived, and the memory 4 stores the plurality of data points and/or the relational equation. As described above, it will be understood by one of ordinary skill in the art that the measurement body part to be measured may be an upper arm, a wrist, a finger, etc. but is not limited thereto. In addition, the plurality of data points used to derive the relational equation may be obtained from body parts of a target subject to be measured, but is not limited thereto. In other words, as will be understood by one of ordinary skill in the art, the body of the target subject (who is to be subjected to blood pressure estimation) and the body of at least one other non-target subject (who is not to be subjected to blood pressure estimation, but instead is used only to provide additional data), or the body of at least one other non-target subject, excluding the target subject, or only the body of the target subject, may be used to obtain the plurality of data points and to derive the relational equation of the plurality of data, wherein the relational equation may be stored in the memory 4. In one embodiment, the memory 4 may be implemented as a separate chip, but is not limited thereto. The memory 4 may be implemented as a device or any device in which a chip is installed to store information. The relational equation may be previously stored in the memory 4 by, for example, upgrading software when or after the blood pressure estimating apparatus 10 is manufactured. A method of deriving the relational equation will be described in more detail below in connection with the estimation unit 5.

The estimation unit 5 calculates variable characteristics ratios according to the shape of the pressure wave measured at the body of the target subject, using the measured blood pressures of the bodies of other non-target subjects, and estimates blood pressure of the target subject using the calculated variable characteristic ratios. The embodiment of an estimation unit 5 includes an operation unit 51, an index determination unit 52, and a blood pressure estimation unit 53. The estimation unit 5 may correspond to one or a plurality of processors of the blood pressure estimating apparatus 10. A processor may be formed using an array of a plurality of logic gates, or a combination of a general-use microprocessor and memory for storing a computer program to be executed in the microprocessor. Also, it will be understood by one of ordinary skill in the art that the processor may be formed using a different type of hardware.

Figure 3:
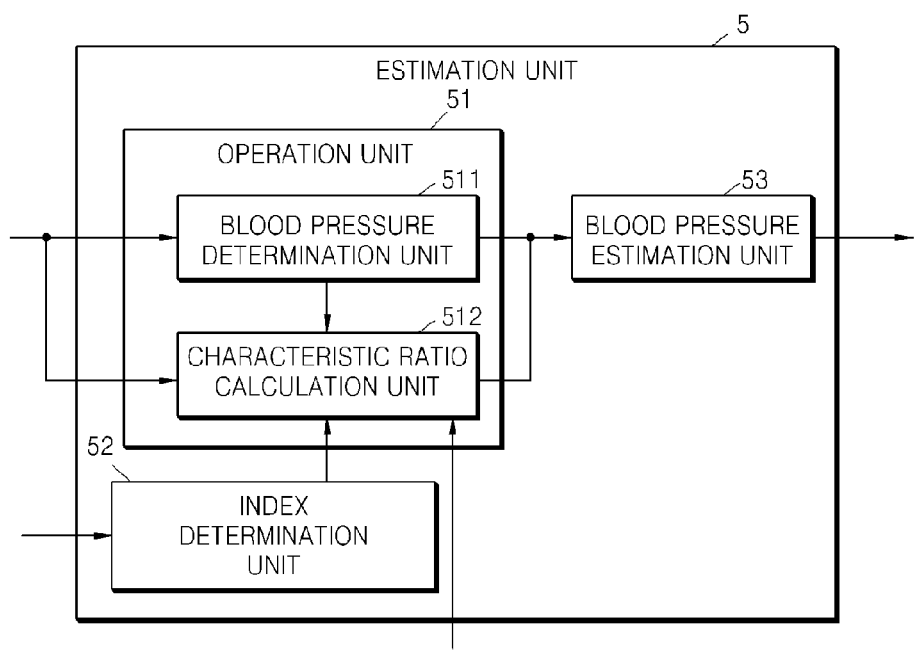
FIG. 3 is a detailed diagram of an estimation unit illustrated in FIG. 1.

The operation unit 51 determines blood pressure using the high-frequency component obtained from the filtering unit 22, and calculates the variable characteristic ratios. FIG. 3 is a detailed diagram of the estimation unit 5 illustrated in FIG. 1. Referring to FIG. 3, the estimation unit 5 includes the operation unit 51, the index determination unit 52 and the blood pressure estimation unit 53. In the present embodiment, the operation unit 51 includes a blood pressure determination unit 511 and a characteristic ratio calculation unit 512.

Figure 4:
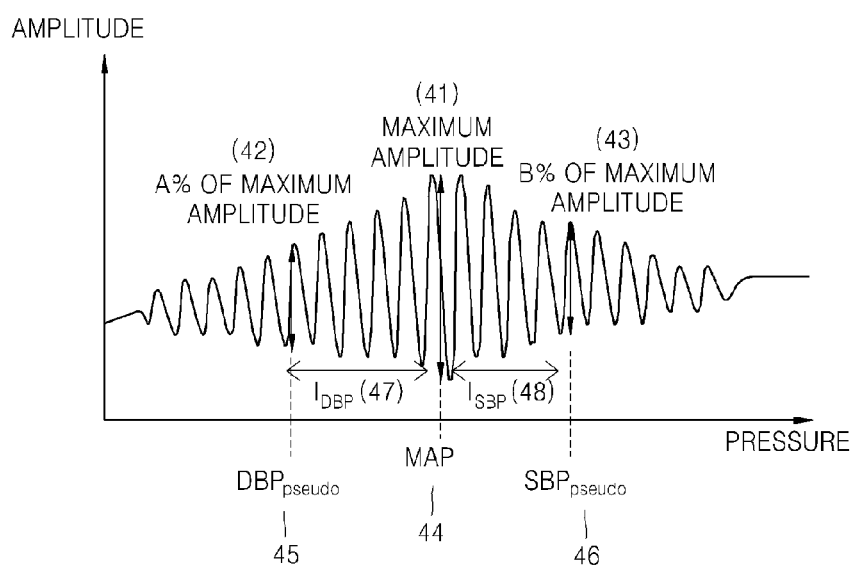
FIG. 4 is a graph of pressures detected at a measurement body part.

FIG. 4 is a graph of pressures detected at a measurement body part. Although an oscillometric method will now be described with reference to FIG. 4 as a blood pressure estimating method, as described above, the blood pressure estimating method is not limited to the oscillometric method. Referring to FIG. 4, the graph illustrates the filtered waveform 241 having the high-frequency components illustrated in FIG. 2 as a graph of amplitude with respect to pressure.

A pressure corresponding to the maximum amplitude 41 of the pressure wave is referred to as a mean arterial pressure ("MAP") 44. The MAP 44 corresponds to pressure at a point of time when pressure applied by the pressing unit 1 is equal to a pressure of a blood vessel sensed by the sensing unit 21. In a general blood pressure measuring apparatus, diastolic blood pressure and systolic blood pressure are determined using a fixed characteristic ratio with respect to the MAP 44 of the pressure wave. The fixed characteristic ratio refers to a ratio used to determine at least one selected from the group consisting of the diastolic blood pressure and the systolic blood pressure, and which is irrespective of the shape of a sensed pressure wave. Hereinafter, in order to distinguish blood pressure calculated using fixed characteristic ratios and blood pressure calculated using variable characteristic ratios, the diastolic blood pressure and the systolic blood pressure, which are calculated using fixed characteristic ratios, are respectively defined as pseudo diastolic blood pressure ("$DBP_{pseudo}$") 45 and pseudo systolic blood pressure ("$SBP_{pseudo}$") 46.

Pressures having specific amplitude ratios with respect to the maximum amplitude 41 may be defined as the diastolic blood pressure and the systolic blood pressure. That is, pressure having a magnitude 42 of A % with respect to the maximum amplitude 41 may be defined as the $DBP_{pseudo}$ 45 and pressure having a magnitude 43 of B % with respect to the maximum amplitude 41 may be defined as the $SBP_{pseudo}$ 46. The fixed characteristic ratios such as A and B may be variously determined by a manufacturer or a user of the blood pressure estimating apparatus 10 illustrated in FIG. 1 according to a usage environment. In one embodiment, the amplitude ratios A and B may be set as 70% and 40%, respectively. That is, pressures having an amplitude with a magnitude of 70% with respect to the maximum amplitude 41 may be defined as the $DBP_{pseudo}$ 45 and pressure having an amplitude with a magnitude of 40% with respect to the maximum amplitude 41 may be defined as the $SBP_{pseudo}$ 46.

Referring back to FIG. 3, the blood pressure determination unit 511 determines at least one selected from the group consisting of the $DBP_{pseudo}$ 45 and the $SBP_{pseudo}$ 46 by using the fixed characteristic ratio, irrespective of the shape of the pressure wave, with respect to the high-frequency component obtained from the filtering unit 22. An embodiment of a method of estimating the $DBP_{pseudo}$ 45 and the $SBP_{pseudo}$ 46 has been described above with reference to FIG. 4, and thus a detailed description thereof will not be provided here.

The characteristic ratio calculation unit 512 calculates a variable characteristic ratio using at least one index obtained from the index determination unit 52 and the relational equation read from the memory 4. Hereinafter, a method of determining an index in the index determination unit 52 will be described in detail.

The index determination unit 52 determines an index for representing the shape of a pressure wave. The shape of a pressure wave represents a reduction rate of amplitude with reference to the maximum amplitude of the pressure wave as the pressure value increases or decreases. For example, in one embodiment the waveform of the pressure wave obtained from the filtering unit 22 may have a bell-like shape. The bell-shaped waveform may become narrow or wide according to the physical characteristics of the target subject from which the pressure wave is sensed. Thus, the index is used to numerically represent the shape of the pressure wave.

The index determination unit 52 determines at least one selected from the group consisting of a systolic blood pressure index $I_{SBP}$ and a diastolic blood pressure index $I_{DBP}$, which are representative values for representing the shape of the pressure wave. In more detail, the index determination unit 52 determines the index using the MAP 44, the $DBP_{pseudo}$ 45, and the $SBP_{pseudo}$ 46. That is, the index determination unit 52 calculates a difference between the MAP 44 and the $SBP_{pseudo}$ 46 and determines the calculated value as the systolic blood pressure index, which is denoted by reference numeral 48. Also, the index determination unit 52 calculates a difference between the MAP 44 and the $DBP_{pseudo}$ 45 and determines the calculated value as the diastolic blood pressure index, which is denoted by reference numeral 47. The index determined by the index determination unit 52 includes the diastolic blood pressure index $I_{DBP}$ and the systolic blood pressure index $I_{SBP}$. Referring to FIG. 4, the diastolic blood pressure index 47 and the systolic blood pressure index 48 may be respectively defined as Equations 1 and 2.

$$I_{DBP} = MAP - DBP_{pseudo} \qquad \text{<Equation 1>}$$

$$I_{SBP} = SBP_{pseudo} - MAP \qquad \text{<Equation 2>}$$

In Equation 1, $I_{DBP}$ denotes the diastolic blood pressure index 47, MAP denotes the MAP 44, and $DBP_{pseudo}$ denotes the $DBP_{pseudo}$ 45. In Equation 2, $I_{SBP}$ denotes the systolic blood pressure index 48, MAP denotes the MAP 44, and $SBP_{pseudo}$ denotes the $SBP_{pseudo}$ 46. Although Equation 1 and the Equation 2 use the $DBP_{pseudo}$ 45 and the $SBP_{pseudo}$ 46 to determine the index, respectively, it is not limited thereto, and an arbitrary pressure on the pressure wave may be used to determine the index, as will be understood by one of ordinary skill in the art.

Referring back to FIG. 3, the characteristic ratio calculation unit 512 calculates a variable characteristic ratio using at least one index and the relational equation. The relational equation defines correlations between expected characteristic ratios of a pressure wave detected at a measurement body part of a non-target subject, which are calculated using reference blood pressures of the non-target subject, and the shape of the pressure wave detected at the measurement body part of the non-target subject. Herein, the reference blood pressure refers to blood pressure of the non-target subject as described above, and may be measured using a noninvasive method or an invasive method. For example, in one embodiment the reference blood pressure may be measured using an invasive method, or using a fixed characteristic ratio while the upper arm of the non-target subject is being pressed. When the reference blood pressure is determined using a noninvasive method, the measurement body part of the non-target subject may be an upper arm, but is not limited thereto.

The measurement body part of the non-target subject may vary according to a blood pressure measuring method used in the blood pressure estimating apparatus 10 in order to provide increased reliability of results. For example, when the blood pressure estimating apparatus 10 estimates blood pressure of a target subject by using a pressure wave detected at a finger of the target subject, the relational equation may be derived using a pressure wave detected at a finger of a non-target subject. In such an embodiment, the reference blood pressure may be measured using an invasive method or a noninvasive method. When a noninvasive method is used, the measurement body part may be an upper arm, a wrist, etc.

The relational equation will now be described in detail. Blood pressure measured at a body part of a non-target subject is set as a reference blood pressure, and characteristic ratios used to determine blood pressure at the body part of the non-target subject are calculated using the reference blood pressure. Next, data representing correlations between the calculate characteristic ratios and indices determined with respect to a pressure wave detected at the body part of the non-target subject are obtained, which is repeatedly performed in order to obtain a plurality of data points. The relational equation is derived from the plurality of data points. In addition, the plurality of data points may be obtained from body parts of at least one non-target subject.

As described above, embodiments include configurations wherein a digital automatic hemadynamometer may use a wrist-type or finger-type blood pressure measuring apparatus in order to measure blood pressure using a noninvasive method. That is, blood pressure is estimated based on a pressure wave detected by pressing a wrist or a finger. However, the blood pressure estimated at a wrist or a finger may be less accurate than the blood pressure estimated at an upper arm having the brachial artery. Thus, blood pressure calculated by applying a fixed characteristic ratio to a pressure wave detected at the upper arm having the brachial artery may be determined as a reference blood pressure, and then estimated characteristic ratios of a pressure wave detected at a wrist having the radial artery may be calculated using the reference blood pressure. The relational equation represents a correlation between such expected characteristic ratios and the shape of the pressure wave.

It will be understood by one of ordinary skill in the art that the reference blood pressure may be measured using an invasive method. For example, the reference blood pressure may be measured at a wrist, the femoral region, etc., of a non-target subject using an invasive method. For example, blood pressure measured at a wrist of a non-target subject using an invasive method may be determined as a reference blood pressure, and then expected characteristic ratios of a pressure wave detected at the wrist of the same non-target subject using a noninvasive method may be calculated using the reference blood pressure.

Figure 5:
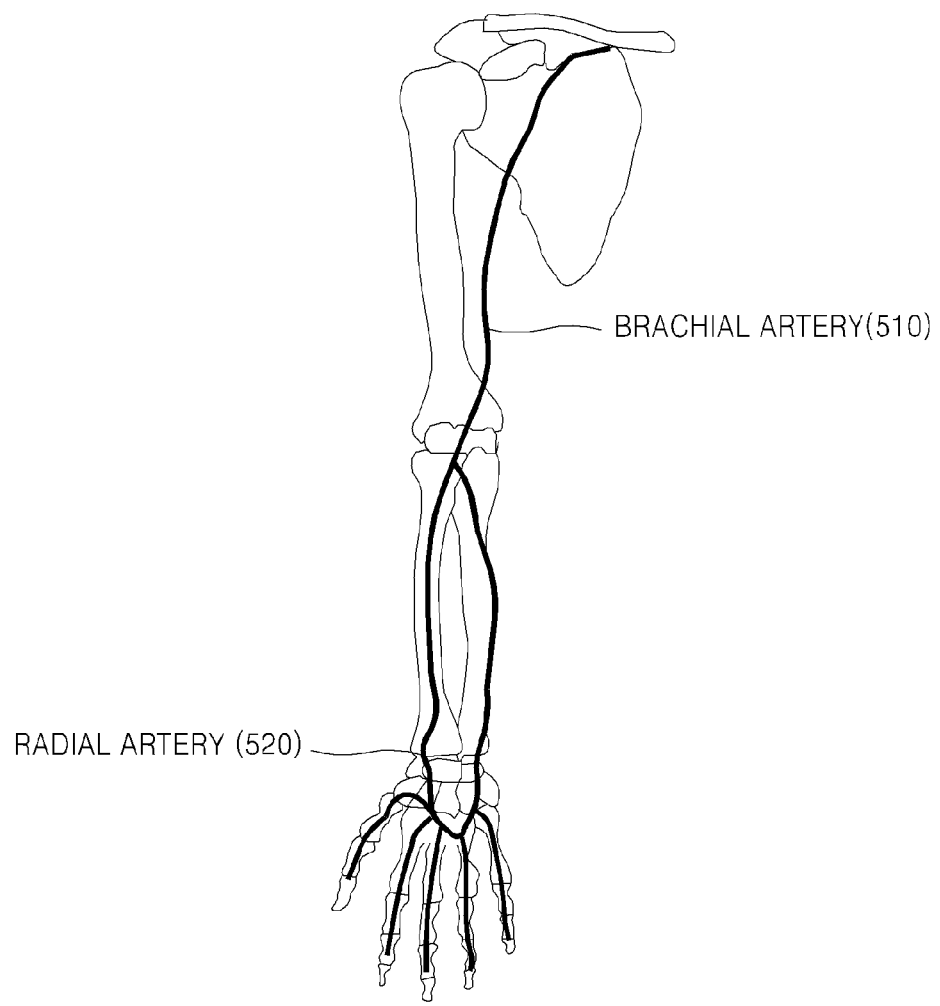
FIG. 5 illustrates the locations of a brachial artery in an upper arm and a radial artery in a wrist.

FIG. 5 illustrates a brachial artery in an upper arm and a radial artery in a wrist. Referring to FIG. 5, the locations of the brachial artery 510 in the upper arm and the radial artery 520 in the wrist are illustrated. If the blood pressure estimating apparatus 10 is a digital wrist-type partial-pressing, blood pressure measuring apparatus, the blood pressure estimating apparatus 10 may estimate blood pressure by applying a fixed characteristic ratio to a pressure wave detected at a wrist having the radial artery 520. If the wrist is locally pressed, an appropriate point of the radial artery 520 for measuring blood pressure may not be easily selected because each subject has unique wrist characteristics (for example, the diameter of a bone, the thickness of the endodermis, fat content, etc. may make location of the appropriate point difficult), and thus accurate blood pressure may not be easily estimated. In addition, since the characteristic ratio varies depending on race, age, physical conditions, arterial elasticity, etc., the accuracy of the automatic blood pressure measuring apparatus may be significantly reduced.

Figure 6:
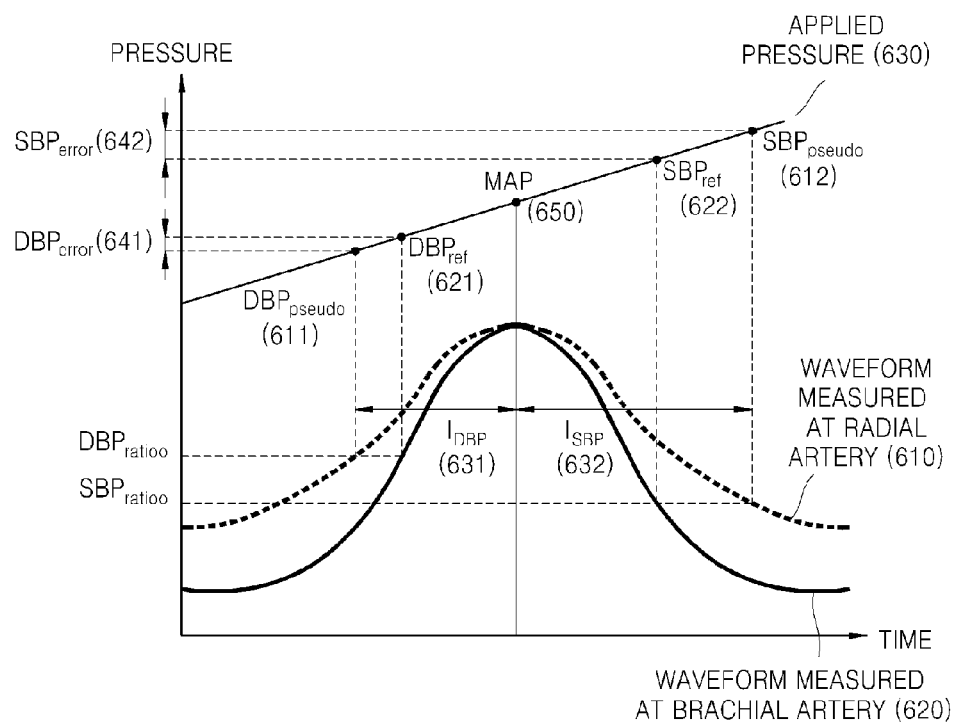
FIG. 6 is a graph of pressures measured at the brachial artery and the radial artery using a noninvasive method.

FIG. 6 is a graph of pressures measured at the brachial artery 510 and the radial artery 520 using a noninvasive method. Referring to FIG. 6, a waveform 610 measured at the radial artery, a waveform 620 measured at the brachial artery, an applied blood pressure 630, a $DBP_{pseudo}$ 611, a $SBP_{pseudo}$ 612, a reference diastolic blood pressure ("$DBP_{ref}$") 621, a reference systolic blood pressure ("$SBP_{ref}$") 622, an $I_{DBP}$ 631, an $I_{SBP}$ 632, a diastolic blood pressure error ("$DBP_{error}$") 641, a systolic blood pressure error ("$SBP_{error}$") 642, and MAP 650 are illustrated.

The waveform 610 measured at the radial artery and the waveform 620 measured at the brachial artery respectively correspond to pressure waves detected at the brachial artery 510 and the radial artery 520 illustrated in FIG. 5. In addition, as illustrated in FIG. 2, the applied pressure 630 is pressure applied to the brachial artery 510 and the radial artery 520. That is, for example, in the blood pressure estimating apparatus 10 illustrated in FIG. 1, the pressing unit 1 presses a body part having blood vessels, with the applied pressure 630, the sensing unit 21 senses pressure values on the walls of the blood vessels, and envelopes of high-frequency components filtered by the filtering unit 22 are calculated, and then normalized to a value of 1 to obtain the waveform 610 measured at the radial artery and the waveform 620 measured at the brachial artery.

An envelope of high-frequency components filtered by the filtering unit 22 may be calculated by dividing the high-frequency components into at least two or more points, and connecting maximum values of the points, wherein in one embodiment the maximum values of the points may be calculated using a Hilbert transformation method. Also, embodiments include configurations wherein the calculated envelope may be reconstructed using a moving average calculation method. A moving average is an average of values calculated at different points to identify a change in a trend. The moving average calculation method is a statistical calculation method in which irregular values of sensed pressures are removed to find a long-term trend. When the moving average is calculated, an average of values calculated at N points is referred to as an N-point moving average. For example, an average of values calculated at three points may be referred to as a three-point moving average. After calculating the envelope and the moving average, for convenience of analysis, each waveform may be normalized to a value of 1. Methods of calculating an envelope, calculating a moving average, and normalizing a waveform are well known to one of ordinary skill in the art, and thus detailed descriptions thereof will not be provided here.

As illustrated in FIG. 6, the waveform 610 measured at the radial artery and the waveform 620 measured at the brachial artery have different shapes, and thus errors may occur in the estimation of diastolic blood pressure and systolic blood pressure unless a correction is applied. In FIG. 6, the waveform 610 measured at the radial artery has a smoother shape than the waveform 620 measured at the brachial artery. This is because the sensing unit 21 may not accurately sense pressure waves due to the resistance of other parts, for example, fat, bones, the epidermis, etc., the difficulty of finding the location of the radial artery, or the inaccuracy of a partial pressing method. Thus, blood pressure calculated using the waveform 620 measured at the brachial artery may be determined as a reference blood pressure, and then expected characteristic ratios of the waveform 610 measured at the radial artery may be calculated using the reference blood pressure. If the blood pressure estimating apparatus 10 uses a wrist-type blood pressure measuring method, the relational equation may be derived by comparing the waveform 620 measured at the brachial artery with the waveform 610 measured at the radial artery, as described above. However, a method of deriving the relational equation is not limited thereto. For example, if the blood pressure estimating apparatus 10 uses a finger-type blood pressure measuring method, the relational equation may be derived by comparing the waveform 620 measured at the brachial artery with a waveform measured at a finger; similarly if the blood pressure estimating apparatus 10 uses any other portion of the body of the subject, the relational equation may be derived by comparing the waveform 620 measured at the brachial artery with a waveform measured at that other portion of a body of the subject.

As described above in relation to FIG. 4, pressures having specific amplitude ratios with respect to the amplitude of the MAP 650 of the waveform 610 measured at the radial artery may be defined as the $DBP_{pseudo}$ 611 and the $SBP_{pseudo}$ 612.

If the fixed characteristic ratios are defined as 70% for the diastolic blood pressure and 40% for the systolic blood pressure, the $DBP_{pseudo}$ 611 and the $SBP_{pseudo}$ 612 are respectively defined at these fixed characteristic ratios. Also, if blood pressure estimated by using the waveform 620 measured at the brachial artery is a reference blood pressure, the reference diastolic blood pressure 621 and the reference systolic blood pressure 622 may be determined using the same fixed characteristic ratios. Thus, the diastolic blood pressure error 641 and the systolic blood pressure error 642 may be respectively defined as Equations 3 and 4.

$$DBP_{error} = DBP_{pseudo} - DBP_{rej} \qquad \langle\text{Equation 3}\rangle$$

$$SBP_{error} = SBP_{pseudo} = SBP_{pseudo} - SBP_{rej} \qquad \langle\text{Equation 4}\rangle$$

In Equation 3, $DBP_{error}$ denotes the diastolic blood pressure error 641, $DBP_{ref}$ denotes the reference diastolic blood pressure 621, and $DBP_{pseudo}$ denotes the pseudo diastolic blood pressure 611 as set forth above. In Equation 4, $SBP_{error}$ denotes the systolic blood pressure error 642, $SBP_{ref}$ denotes the reference systolic blood pressure 622, and $SBP_{pseudo}$ denotes the pseudo systolic blood pressure 612 as set forth above. Thus, when blood pressure is determined by applying a fixed characteristic ratio to the pressure waves that are measured at the brachial artery 510 and the radial artery 520 of one subject using a noninvasive method, the calculated blood pressures are not the same. Since the shape of a pressure wave depends on race, age, gender, physical conditions, arterial elasticity, etc., blood pressure may not be accurately estimated using a fixed characteristic ratio, but rather may be accurately estimated using a variable characteristic ratio.

With regard to a method of calculating a variable characteristic ratio, an expected characteristic ratio used to determine blood pressure at a measurement body part is calculated using a reference blood pressure, and then the variable characteristic ratio is calculated based on a correlation between the expected calculated characteristic ratio and an index representing the shape of the pressure wave measured at the body part. The reference blood pressure may be measured using an invasive method or a noninvasive method. However, a higher degree of accuracy is used for the reference blood pressure than the blood pressure measured at the measurement body part. Thus, the reference blood pressure may be measured using an invasive method in order to generate the highest degree of accuracy, although the disclosure is not limited thereto. Also, when the reference blood pressure is measured using a noninvasive method, it may be calculated by applying a fixed characteristic ratio to the pressure wave measured at the brachial artery 510.

Figure 7:
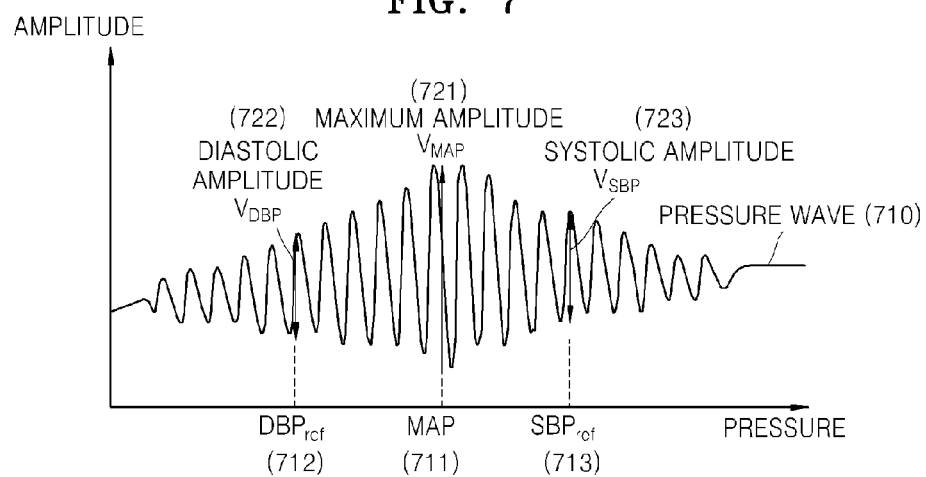
FIG. 7 is a graph illustrating an embodiment of a method of calculating a characteristic ratio of a pressure wave using a reference blood pressure.

FIG. 7 is a graph for explaining an embodiment of a method of calculating a characteristic ratio of a pressure wave using a reference blood pressure. Referring to FIG. 7, a pressure wave 710 measured at a measurement body part, a MAP 711 having the maximum amplitude of the pressure wave, $DBP_{ref}$ 712 measured using an invasive method, $SBP_{ref}$ 713 measured using the invasive method, the maximum amplitude ("$V_{MAP}$") 721 of the pressure wave measured at the measurement body part, a diastolic amplitude ("$V_{DBP}$") 722 at an expected diastolic characteristic ratio, and a systolic amplitude ("$V_{SBP}$") 723 at a systolic expected characteristic ratio are illustrated. Although the $DBP_{ref}$ 712 and the $SBP_{ref}$ 713 may be measured using the invasive method in one embodiment, for convenience of explanation, it will be understood by one of ordinary skill in the art that the $DBP_{ref}$ 712 and the $SBP_{ref}$ 713 may be measured at the brachial artery of the upper arm using a noninvasive method in another embodiment.

The $V_{DBP}$ 722 refers to an amplitude of the pressure wave 710 measured at the measurement body part corresponding to the $DBP_{ref}$ 712, and the $V_{SBP}$ 723 refers to an amplitude of the pressure wave 710 measured at the measurement body part corresponding to $SBP_{ref}$ 713. A diastolic characteristic ratio DBP ratio and a systolic characteristic ratio $SBP_{ratio}$ calculated using the respective $DBP_{ref}$ 712 and $SBP_{ref}$ 713 may be respectively defined according to Equations 5 and 6.

$$DBP_{ratio} = \frac{V_{DBP}}{V_{MAP}} \qquad \langle\text{Equation 5}\rangle$$

$$SBP_{ratio} = \frac{V_{SBP}}{V_{MAP}} \qquad \langle\text{Equation 6}\rangle$$

In Equation 5, $DBP_{ratio}$ denotes the diastolic characteristic ratio, $V_{DBP}$ denotes the diastolic amplitude 722 corresponding to the $DBP_{ref}$, and $V_{MAP}$ denotes the maximum amplitude 721. In Equation 6, $SBP_{ratio}$ denotes the systolic characteristic ratio, $V_{SBP}$ denotes the systolic amplitude 723 corresponding to the $SBP_{ref}$, and $V_{MAP}$ denotes the maximum amplitude 721. A correlation between the $DBP_{ratio}$ calculated using Equation 5 and the $I_{DBP}$ of the pressure wave, which is measured at the measurement body part and determined using Equation 1, and a correlation between the $SBP_{ratio}$ calculated using Equation 6 and the $I_{SBP}$ of the pressure wave, which is measured at the measurement body part and determined by using Equation 2, may be plotted.

Figure 8A:
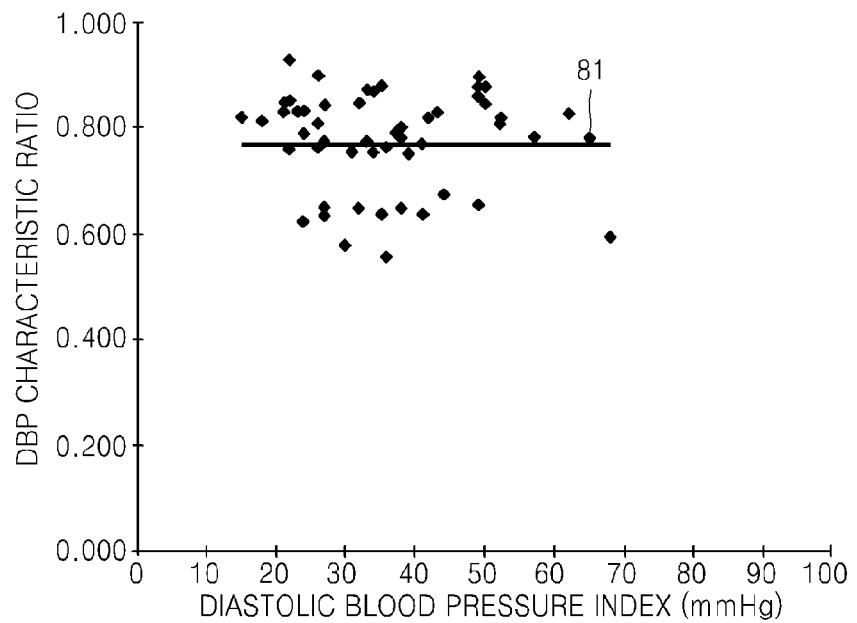
FIG. 8A is a graph of correlation between a diastolic blood pressure index ("$I_{DBP}$") and a diastolic characteristic ratio ("$DBP_{ratio}$")
Figure 8B:
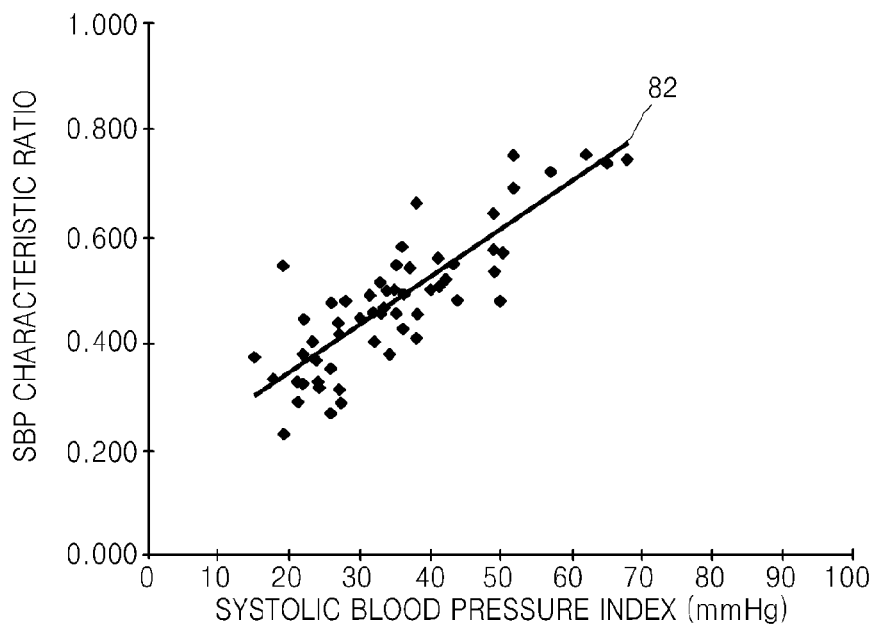
FIG. 8B is a graph of correlation between a systolic blood pressure index ("$I_{SBP}$") and a systolic characteristic ratio ("$SBP_{ratio}$")

FIGS. 8A and 8B are graphs showing correlations between indices and characteristic ratios. FIG. 8A is a graph of correlation between the $I_{DMP}$ and the $DBP_{ratio}$, and FIG. 8B is a graph of correlation between the $I_{SBP}$ and the $SBP_{ratio}$. A diastolic blood pressure index-characteristic ratio correlation trend line 81 is illustrated in FIG. 8A, and a systolic blood pressure index-characteristic ratio correlation trend line 82 is illustrated in FIG. 8B.

The diastolic and systolic blood pressure indices ($I_{DBP}$ and $I_{SBP}$), and the diastolic and systolic characteristic ratios ($DBP_{ratio}$ and $SBP_{ratio}$) are calculated using Equations 1 and 2, and Equations 5 and 6, respectively, and the calculated results are plotted in FIGS. 8A and 8B, respectively, as the diastolic blood pressure index-characteristic ratio correlations 81 and the systolic blood pressure index-characteristic ratio correlations 82. In FIGS. 8A and 8B, a dot is a result of calculating the diastolic or systolic blood pressure index and the diastolic or systolic characteristic ratio from one-time blood pressure measurement. Thus, the calculations using Equations 1 and 2, and Equations 5 and 6 are repeated, and the results are used to derive the relational equation.

The diastolic blood pressure index-characteristic ratio correlation trend line 81 and the systolic blood pressure index-characteristic ratio correlation trend line 82 may be calculated by applying various algorithms based on statistical methods to the diastolic blood pressure index-characteristic ratio correlations and the systolic blood pressure index-characteristic ratio correlations. Trend line calculation is performed in order to analyze a trend in variations and embodiments may be performed using, for example, a least mean square ("LMS") algorithm. For example, according to the LMS algorithm, the diastolic blood pressure index-characteristic ratio correlation trend line 81 is defined so that each of the diastolic blood pressure index-characteristic ratio correlations has a minimum difference from the diastolic blood pressure index-characteristic ratio correlation trend line 81. The diastolic blood pressure index-characteristic ratio correlation trend line 81 and the systolic blood pressure index-characteristic ratio correlation trend line 82 may be defined according to Equations 7 and 8, respectively.

$$\text{ExpDBP}_{ratio} = \alpha(I_{DBP}) + \beta \qquad \text{<Equation 7>}$$

$$\text{ExpSBP}_{ratio} = \gamma(I_{SBP}) + \delta \qquad \text{<Equation 8>}$$

In Equation 7, $\text{ExpDBP}_{ratio}$ denotes an expected diastolic blood pressure characteristic ratio. In Equation 8, $\text{ExpSBP}_{ratio}$ denotes an expected systolic blood pressure characteristic ratio. Also, $\alpha$, $\beta$, $\gamma$, and $\delta$ are values calculated using a trend line calculation method. For example, $\alpha$, $\beta$, $\gamma$, and $\delta$ may be set as $\alpha = -0.0001$, $\beta = 1$, $\gamma = 0.009$, and $\delta = 0.5$ in the present embodiment. Thus, the expected diastolic blood pressure characteristic ratio $\text{ExpDBP}_{ratio}$ may be calculated using the diastolic blood pressure index $I_{DBP}$ and the diastolic blood pressure index-characteristic ratio correlation trend line 81, which is defined by Equation 7. Also, the expected systolic blood pressure characteristic ratio $\text{ExpSBP}_{ratio}$ may be calculated using the systolic blood pressure index $I_{SBP}$, and the systolic blood pressure index-characteristic ratio correlation trend line 82, which is defined by Equations 8. The expected diastolic blood pressure characteristic ratio $\text{ExpDBP}_{ratio}$ and the expected systolic blood pressure characteristic ratio $\text{ExpSBP}_{ratio}$, which are calculated by using the $I_{DBP}$ and the $I_{SBP}$ to represent the pressure wave measured at the measurement body part, may be defined as variable characteristic ratios of the pressure wave measured at the measurement body part. In other words, the variable characteristic ratios, which are adaptive to the shape of the pressure wave, may be calculated using the $I_{DBP}$ and the $I_{SBP}$, which represent the shape of the pressure wave measured at the measurement body part.

Equations 7 and 8 are referred to as relational equations, which may be previously stored in the memory 4. However, Equations 7 and 8 are only examples of relational equations, and other relational equations may be calculated using a trend line calculation method based on statistical methods, as described above.

Referring back to FIG. 3, the blood pressure estimation unit 53 estimates at least one blood pressure having an amplitude corresponding to the calculated variable characteristic ratio with respect to the maximum amplitude of the pressure wave measured at the body part of the target subject being pressed. Here, the estimated blood pressure may include at least one selected from the group consisting of the diastolic blood pressure and the systolic blood pressure. Blood pressure of the target subject may be estimated according to the embodiment of a method described with reference to FIG. 4, e.g., using the calculated variable characteristic ratio.

The output unit 6 displays the blood pressure output from the estimation unit 5 to the user. In the present embodiment, the output unit 6 includes both a device for displaying visual information, such as a display device embodiments of which may include a liquid crystal display ("LCD") screen, a light-emitting diode ("LED"), or a division display device, and/or a device for providing auditory information, such as a speaker, in order to display information to the user.

Figure 9:
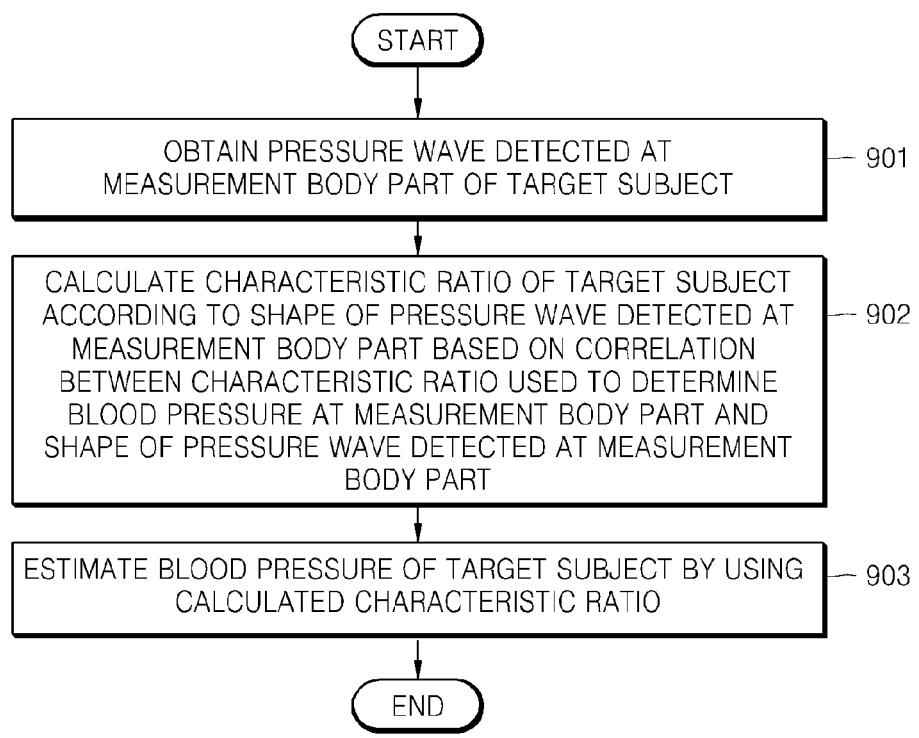
FIG. 9 is a flowchart of an embodiment of a method of estimating blood pressure using a variable characteristic ratio.

FIG. 9 is a flowchart of an embodiment of a method of estimating blood pressure using a variable characteristic ratio. The method of estimating blood pressure includes operations performed sequentially in the embodiment of a blood pressure estimating apparatus 10 in FIG. 1. Therefore, although not explicitly described in the flowchart, the content described above in connection with the blood pressure estimating apparatus 10 in FIG. 1 also applies to the method of estimating blood pressure.

In operation 901, the estimation unit 5 obtains a pressure wave detected at a measurement body part of a target subject. That is, the sensing unit 21 senses the pressure wave while the measurement body part of the target subject is being pressed, the filtering unit 22 filters the high-frequency component of the sensed pressure wave and transmits the filtered high-frequency component to the estimation unit 5. Herein, the sensing unit 21 may include at least one sensor. Although a pressure sensor, a PPG sensor, or other similar components may be generally used as the sensor, the sensing unit 21 is not limited thereto. For example, in one embodiment the sensing unit 21 may be any apparatus for detecting pressure waves in a blood vessel. Also, as described above, it will be understood by one of ordinary skill in the art that the measurement body part may be a wrist, a finger, or the like, but is not limited thereto.

In operation 902, a characteristic ratio of the target subject according to the shape of the pressure wave obtained in operation 901 is calculated based on a correlation between a characteristic ratio used to determine blood pressure at the measurement body part of a non-target subject and a shape of the pressure wave detected at the measurement body part. Herein, the characteristic ratio used to determine blood pressure at the measurement body part of the non-target subject may be determined using a reference blood pressure of the non-target subject, wherein the reference blood pressure may be measured using an invasive method or a noninvasive method.

In operation 903, the blood pressure estimation unit 53 estimates blood pressure of the target subject using the calculated characteristic ratio. The estimated blood pressure may be displayed to a user by the output unit 6.

Figure 10:
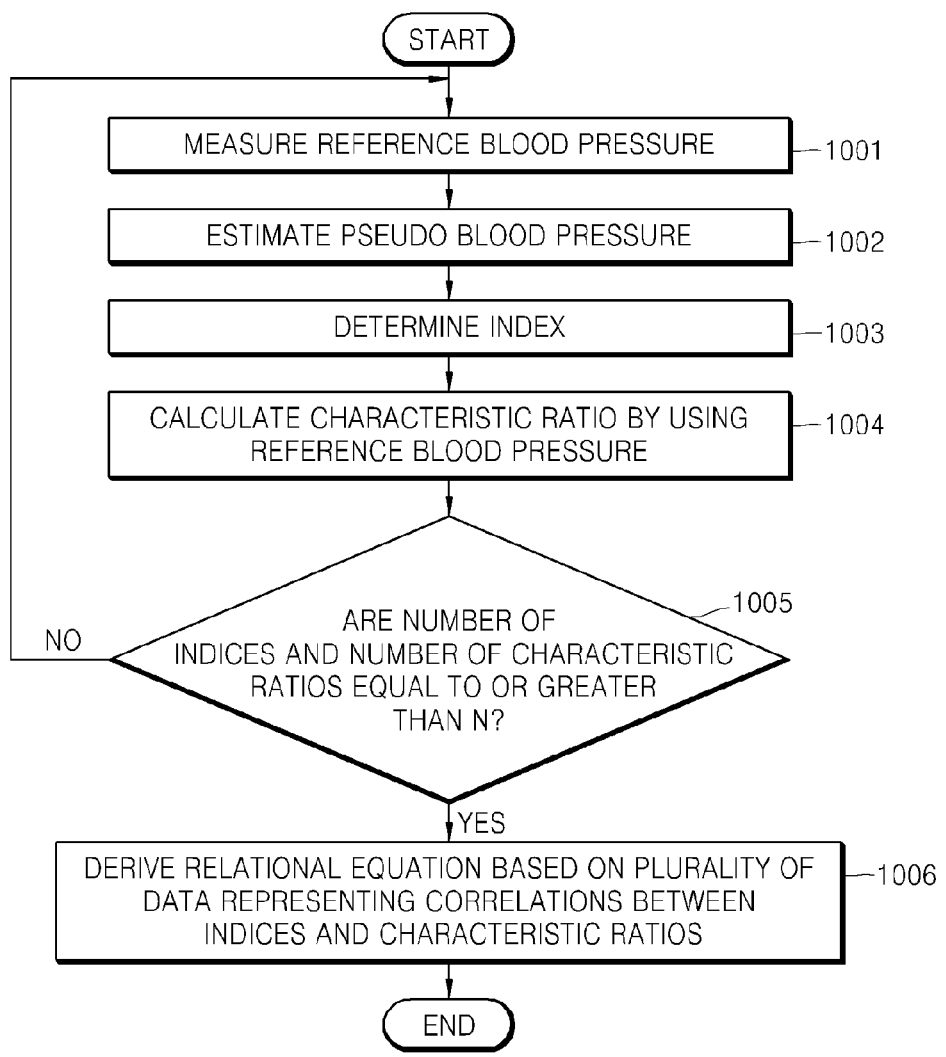
FIG. 10 is a flowchart of an embodiment of a method of deriving a relational equation for calculating a variable characteristic ratio.

FIG. 10 is a flowchart of an embodiment of a method of deriving a relational equation for calculating a variable characteristic ratio. In addition, data points used to derive the relational equation may be obtained from body parts of the target subject, but is not limited thereto. For example, the data points may be obtained from body parts of a number of non-target subjects unrelated to blood pressure estimation.

In operation 1001, a reference blood pressure is measured at a body part of a non-target subject using an invasive method or a noninvasive method having high accuracy. The reference blood pressure may include at least one selected from the group consisting of a $\text{DBP}_{ref}$ and a $\text{SBP}_{ref}$. When measuring the reference blood pressure by using a noninvasive method, a fixed characteristic ratio that is generally used may be used.

In operation 1002, a pseudo blood pressure is estimated at the measurement body part. For example, the pseudo blood pressure may be determined by applying a fixed characteristic ratio to a pressure wave measured at the radial artery of a wrist. Herein, the fixed characteristic ratio is the same as used in operation 1001 above. The pseudo blood pressure includes at least one of a $\text{DBP}_{pseudo}$ and a $\text{SBP}_{pseudo}$.

In operation 1003, an index is determined. The index is defined as a difference between blood pressure having a maximum amplitude of the pressure wave measured at the measurement body part of the non-target subject, and the pseudo blood pressure. The index includes at least one selected from the group consisting of the $I_{DBP}$ and the $I_{SBP}$. For example, in one embodiment the index may be determined using a difference between blood pressure having a maximum amplitude of the pressure wave measured at the radial artery of the wrist and the pseudo blood pressure calculated in operation 1002.

In operation 1004, a characteristic ratio used to determine blood pressure at the measurement body part of the non-target subject is calculated using the reference blood pressure. For example, the $DBP_{ratio}$ used to determine diastolic blood pressure may be defined as a ratio of an amplitude corresponding to the $DBP_{ref}$ with respect to the maximum amplitude of the pressure wave, and the $SBP_{ratio}$ used to determine systolic blood pressure may be defined as a ratio of an amplitude corresponding to the $SBP_{ref}$ with respect to the maximum amplitude of the pressure wave.

In operation 1005, if the number of indices determined in operation 1003 and the number of characteristic ratios calculated in operation 1004 are equal to or greater than n (wherein n is a natural number), the method proceeds to operation 1006. Otherwise, the method returns to operation 1001. N may be an arbitrary number set by a user according to a usage environment. As n increases, the accuracy of the derived relational equation may be increased. For example, when n=60, the accuracy of the derived relational equation may be very accurate. However, when operations 1001 through 1004 are repeatedly performed, the measurement body part may be not limited to a body part of one subject. In other words, operations 1001 through 1004 may be repeatedly performed on at least one non-target subject in order to collect data. The at least one non-target subject may be different from each other in terms of age, gender, physical conditions, height, weight, or other attributes. Alternatively, the operations may be performed on a group of subjects satisfying a specific condition in order to derive a relational equation only for the group of subjects satisfying the specific condition.

In operation 1006, a trend line is calculated based on the plurality of data points representing correlations between the indices and the characteristic ratios, and the indices determined in operation 1003 and the characteristic ratios calculated in operation 1004. The trend line is calculated using an algorithm so that each characteristic ratio regarding an index has a minimum difference from the calculated trend line. The calculated trend line corresponds to a relational equation and may be stored in the memory 4 of the blood pressure estimating apparatus 10.

Figure 11:
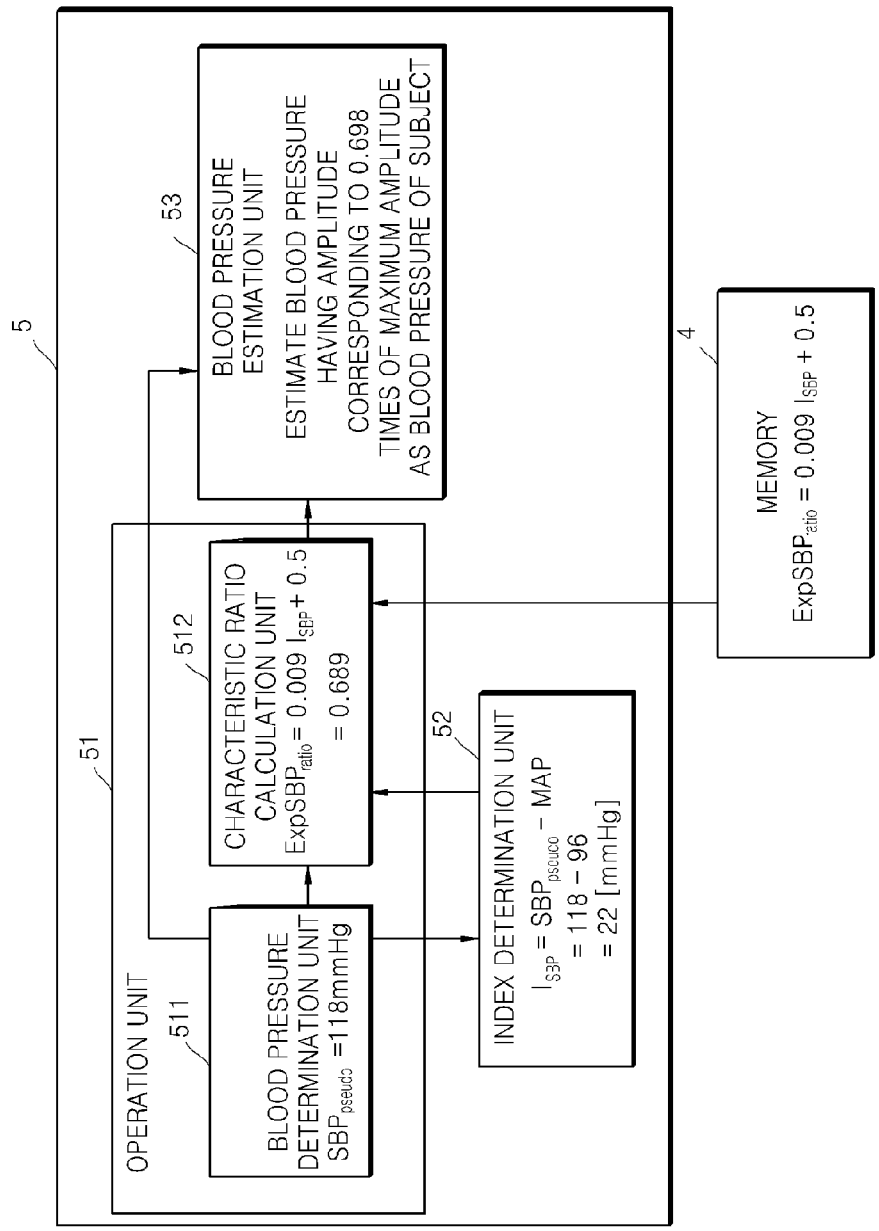
FIG. 11 is a diagram describing an embodiment of a method of estimating systolic blood pressure.

FIG. 11 is a diagram for describing estimating systolic blood pressure. Referring to FIG. 11, for convenience of explanation, only systolic blood pressure will be described. However, it will be understood by one of ordinary skill in the art that blood pressure to be estimated is not limited thereto, and may include diastolic blood pressure and/or another type of blood pressure. It is assumed for this discussion that the memory 4 have previously stored a relational equation as determined above for calculating the systolic characteristic ratio. The relational equation may be derived according to the flowchart illustrated in FIG. 10. The relational equation for calculating the systolic characteristic ratio illustrated in FIG. 11 is as defined in Equation 8. Hereinafter, for convenience of explanation, the relational equation for estimating systolic blood pressure may be further defined as shown in Equation 9.

$$ExpSBP_{ratio}=0.009(I_{SBP})+0.5 \qquad <\text{Equation 9}>$$

The blood pressure determination unit 511 determines $SBP_{pseudo}$ by applying a fixed characteristic ratio to the pressure wave detected at a measurement body part of a target subject. For example, in one embodiment the $SBP_{pseudo}$ is 118 mmHg.

The index determination unit 52 determines a difference between the SBP pseudo and blood pressure having a maximum amplitude of the pressure wave detected at the measurement body part of the target subject (i.e., MAP), as an $I_{SBP}$. For example, if the MAP is 96 mmHg and the $SBP_{pseudo}$ is 118 mmHg, the $I_{SBP}$ is 22 mmHg.

The characteristic ratio calculation unit 512 calculates an $ExpSBP_{ratio}$ using the $I_{SBP}$ and the relational equation (e.g., Equation 9) read from the memory 4. According to Equation 9, the $ExpSBP_{ratio}$, i.e., a variable characteristic ratio, is about 0.698.

The blood pressure estimation unit 53 estimates blood pressure having an amplitude corresponding to 0.698 times the maximum amplitude of the pressure wave detected at the measurement body part of the target subject as the systolic blood pressure of the target subject. The estimated blood pressure may be displayed to a user by the output unit 6.

As described above, the blood pressure estimating apparatus 10 may calculate a characteristic ratio that varies according to the shape of a pressure wave detected at a measurement body part of a target subject, and may improve accuracy in blood pressure estimation using the calculated characteristic ratio. A pressure wave may be conveniently measured at a wrist or a finger using a noninvasive method, and blood pressure may be accurately estimated using the variable characteristic ratio. Thus, convenient accurate blood pressure measurement is ensured.

As described above, an embodiment of a blood pressure estimating apparatus using a noninvasive blood pressure measurement method may improve accuracy in blood pressure estimation using a characteristic ratio that varies according to the physical and physiological characteristics of a target subject. Thus, blood pressure may be conveniently and accurately measured. In addition, in a finger-type or wrist-type, partial pressing, blood pressure measuring apparatus, blood pressure may be accurately and conveniently measured.

The apparatus and method for estimating blood pressure by using a variable characteristic ratio may be written as computer programs and may be implemented in general-use digital computers that execute the programs using a computer readable recording medium. Data used in the above-described examples may be recorded on a medium in various means. Examples of the computer readable recording medium include magnetic storage media (e.g., random access memory ("ROM"), floppy disks, hard disks, etc.) and optical recording media (e.g., CD-ROMs, or DVDs).

While this invention has been particularly shown and described above, it will be understood by those of ordinary skill in the art that various changes in form and details may be made therein without departing from the spirit and scope of the invention as defined by the appended claims.

What is claimed is:

1. A method of estimating blood pressure, the method comprising:
    obtaining, by at least one sensor, a pressure wave detected at a measurement body part of a subject and a reference pressure wave detected at a reference measurement body part of the subject which is different from the measurement body part;
    determining, by at least one processor, an index to be a difference between a blood pressure determined by applying a fixed characteristic ratio and a blood pressure having a maximum amplitude of the detected pressure wave which is transmitted by the at least one sensor;

calculating, by at least one processor, a reference characteristic ratio using the detected reference pressure wave which is transmitted by the at least one sensor;

calculating, by at least one processor, a variable characteristic ratio based on a correlation between the determined index and the reference characteristic ratio;

estimating, by at least one processor, blood pressure at the measurement body part of the subject using the calculated variable characteristic ratio; and outputting, by an output unit, the blood pressure at the measurement body part of the subject, wherein the fixed characteristic ratio comprises a characteristic ratio which is fixed and irrespective of the shape of the pressure wave, wherein the variable characteristic ratio comprises a characteristic ratio which is a calculated characteristic ratio of the subject and variable according to the shape of the obtained pressure wave, and wherein the reference characteristic ratio comprises a characteristic ratio which is used to determine blood pressure at a measurement body part and determined using a reference blood pressure measured at the reference measurement body part.

2. The method of claim 1, wherein the shape of the pressure wave represents a rate of amplitude reduction with reference to a pressure value having a maximum amplitude as the pressure value one of increases and decreases.

3. The method of claim 1, wherein the reference blood pressure comprises at least one selected from the group consisting of a diastolic blood pressure and a systolic blood pressure, which are determined by applying the fixed characteristic ratio used to determine the blood pressure, irrespective of the shape of the pressure wave, to a pressure wave detected while an upper arm of the measurement body part is pressed.

4. The method of claim 1, wherein the reference blood pressure is measured using an invasive method.

5. The method of claim 1, wherein the index represents the shape of the detected pressure wave.

6. The method of claim 5, wherein the calculating of the variable characteristic ratio according to the shape of the obtained pressure wave includes applying the determined index to a relational equation derived using a plurality of data representing the correlation.

7. The method of claim 5, wherein the estimating of the blood pressure includes at least one blood pressure having an amplitude corresponding to the calculated variable characteristic ratio with respect to the maximum amplitude of the pressure wave detected while the measurement body part of the subject is pressed is estimated as the blood pressure of the subject.

8. The method of claim 5, further comprising
determining a pseudo diastolic blood pressure by applying the fixed characteristic ratio, irrespective of the shape of the pressure wave, to the pressure wave detected at the measurement body part of the subject, wherein determining the index includes subtracting the determined pseudo diastolic blood pressure from the blood pressure having the maximum amplitude of the pressure wave detected at the measurement body part of the subject to determine a diastolic blood pressure index, wherein the calculating of the variable characteristic ratio includes calculating a diastolic characteristic ratio, wherein the estimating of the blood pressure at the measurement body part of the subject includes estimating a blood pressure having an amplitude corresponding to the calculated diastolic characteristic ratio with respect to the maximum amplitude of the pressure wave to be the diastolic blood pressure of the subject, and wherein the diastolic characteristic ratio comprises a characteristic ratio which is used to determine a diastolic blood pressure of the subject using the determined diastolic blood pressure index.

9. The method of claim 5, further comprising determining a pseudo systolic blood pressure by applying the fixed characteristic ratio, irrespective of the shape of the pressure wave, to the pressure wave detected at the measurement body part of the subject, wherein determining the index includes subtracting the blood pressure having the maximum amplitude of the pressure wave detected at the measurement body part of the subject from the determined pseudo systolic blood pressure to determine a systolic blood pressure index, wherein calculating the variable characteristic ratio includes calculating a systolic characteristic ratio, wherein the estimating of the blood pressure at the measurement body part of the subject includes estimating a pressure having an amplitude corresponding to the calculated systolic characteristic ratio of the subject with respect to the maximum amplitude of the pressure wave to be the systolic blood pressure of the subject, and wherein the systolic characteristic ratio comprises a characteristic ratio which is used to determine a systolic blood pressure of the subject using the determined systolic blood pressure index.

10. A non-transitory computer readable recording medium having embodied thereon a program for executing the method of claim 1.

11. A blood pressure estimating apparatus comprising:
at least one sensor configured to detect a pressure wave at a measurement body part of a subject and a reference pressure wave detected at a reference measurement body part of the subject which is different from the measurement body part;

an index determination processor configured to determine a difference between a blood pressure determined by applying a fixed characteristic ratio and a blood pressure having a maximum amplitude of the detected pressure wave which is transmitted by the at least one sensor;

a characteristic ratio calculation processor configured to calculate a reference characteristic ratio based on the detected reference pressure wave which is transmitted by the at least one sensor, and to calculate the variable characteristic ratio based on a determined index and a correlation between the determined index and the reference characteristic ratio;

a blood pressure estimating processor configured to estimate blood pressure at the measurement body part of the subject using the calculated variable characteristic ratio; and an output unit configured to output the blood pressure at the measurement body part of the subject, wherein the fixed characteristic ratio comprises a characteristic ratio which is fixed and irrespective of the shape of the pressure wave, wherein the variable characteristic ratio comprises a characteristic ratio which is a calculated characteristic ratio of the subject, and variable according to the shape of the obtained pressure wave, and wherein the reference characteristic ratio comprises a characteristic ratio which is used to determine blood pressure at a measurement body part and determined using a reference blood pressure measured at the reference measurement body part.

12. The apparatus of claim 11, wherein the shape of the pressure wave represents a rate of amplitude reduction with reference to a pressure value having a maximum amplitude as the pressure value one of increases and decreases.

13. The apparatus of claim 11, wherein the reference blood pressure comprises at least one selected from the group consisting of a diastolic blood pressure and a systolic blood pressure, which are determined by applying the fixed characteristic ratio used to determine the blood pressure, irrespective of the shape of the pressure wave, to a pressure wave detected while an upper arm of the measurement body part is pressed.

14. The apparatus of claim 11, wherein the reference blood pressure is measured using an invasive method.

15. The apparatus of claim 11, wherein the index represents the shape of the detected pressure wave.

16. The apparatus of claim 15, wherein the variable characteristic ratio calculation processor calculates the variable characteristic ratio by applying the determined index to a relational equation derived using a plurality of data points representing the correlation.

17. The apparatus of claim 15, wherein the blood pressure estimation processor estimates at least one blood pressure having an amplitude corresponding to the calculated variable characteristic ratio with respect to the maximum amplitude of the pressure wave detected while the measurement body part of the subject is pressed, to be the blood pressure of the subject.

18. The apparatus of claim 15, further comprising:
a blood pressure determination processor configured to determine a pseudo systolic blood pressure by applying the fixed characteristic ratio, irrespective of the shape of the pressure wave, to the pressure wave detected at the measurement body part of the subject,
wherein the index determination processor configured to determine a result of subtracting the blood pressure having the maximum amplitude of the pressure wave detected at the measurement body part of the subject from the determined pseudo systolic blood pressure to be a systolic blood pressure index,
wherein the variable characteristic ratio calculation processor configured to calculate a diastolic characteristic ratio used to determine a systolic blood pressure of the subject using the determined systolic blood pressure index,
wherein the blood pressure estimation processor configured to estimate a pressure having an amplitude corresponding to the calculated diastolic characteristic ratio of the subject with respect to the maximum amplitude of the pressure wave to be the systolic blood pressure of the subject, and
wherein the diastolic characteristic ratio comprises a characteristic ratio which is used to determine a systolic blood pressure of the subject using the determined systolic blood pressure index.

* * * * *